(12) United States Patent
Prat

(10) Patent No.: US 12,132,379 B2
(45) Date of Patent: Oct. 29, 2024

(54) MOTORISED RESPIRATORY ASSISTANCE DEVICE, WITH DOUBLE COOLING OF THE MOTOR EQUIPPING THE DEVICE

(71) Applicant: AIRFAN, Colomiers (FR)

(72) Inventor: Xavier Prat, Villeneuve Tolosane (FR)

(73) Assignee: AIRFAN, Colomiers (FR)

( * ) Notice: Subject to any disclaimer, the term of this patent is extended or adjusted under 35 U.S.C. 154(b) by 378 days.

(21) Appl. No.: 17/755,003

(22) PCT Filed: Oct. 12, 2020

(86) PCT No.: PCT/EP2020/078590
§ 371 (c)(1),
(2) Date: Apr. 19, 2022

(87) PCT Pub. No.: WO2021/083646
PCT Pub. Date: May 6, 2021

(65) Prior Publication Data
US 2022/0360143 A1    Nov. 10, 2022

(30) Foreign Application Priority Data
Oct. 31, 2019   (FR) .................................. FR1912294

(51) Int. Cl.
*H02K 9/06*         (2006.01)
*H02K 5/20*         (2006.01)
(Continued)

(52) U.S. Cl.
CPC .................. *H02K 9/06* (2013.01); *H02K 5/20* (2013.01); *H02K 7/14* (2013.01); *H02K 9/14* (2013.01)

(58) Field of Classification Search
CPC .. H02K 9/06; H02K 9/14; H02K 7/14; H02K 5/20; H02K 5/207; H02K 9/16
See application file for complete search history.

(56) References Cited

U.S. PATENT DOCUMENTS 6,164,084 A * 12/2000 Watson .................. H02K 5/207
                                                                    310/60 R
2009/0291004 A1* 11/2009 Grasmuck ................ H02K 5/12
                                                                    417/423.1
2016/0352181 A1* 12/2016 Randria .................... H02K 9/16

FOREIGN PATENT DOCUMENTS

EP          2122180       6/2017
FR          2910079       6/2008
(Continued)

*Primary Examiner* — Tulsidas C Patel
*Assistant Examiner* — Robert E Mates
(74) *Attorney, Agent, or Firm* — Defillo & Associates, Inc; Evelyn A. Defillo

(57) ABSTRACT

A motorised respiratory assistance device with an integrated cooling system including an enclosure (1) forming a compartment (2) accommodating a motor unit (3) driving turbines (8a, 8b) generating a main respiratory assistance air flow (F1) and a secondary air flow (F2) for cooling the motor (5). The secondary air flow (F2) is conveyed by a secondary aeraulic path (E2, E4, E5, 22, E3, S2) that includes an inner portion (E2, E4, E5, 22) extending into the motor (5) between the stator (6a) and the rotor (6b) and an outer portion (E3, S2) that extends into an annular space (E3) provided around the motor unit (3). The cooling air flow (F2) flows in opposing directions in the inner (E4) and outer (E3) portions, and the main aeraulic path (E1, E6, S1) and the secondary aeraulic path (E2, E4, E5, 22, E3, S2) are separated from each other by a partition (18).

13 Claims, 3 Drawing Sheets

(51) Int. Cl.
*H02K 7/14* (2006.01)
*H02K 9/14* (2006.01)

(56) References Cited

FOREIGN PATENT DOCUMENTS

| | | |
|---|---|---|
| FR | 2910081 | 6/2008 |
| FR | 3057464 | 4/2018 |
| WO | WO2018073275 | 4/2018 |

* cited by examiner

MOTORISED RESPIRATORY ASSISTANCE DEVICE, WITH DOUBLE COOLING OF THE MOTOR EQUIPPING THE DEVICE

CROSS REFERENCE TO RELATED APPLICATION

This application is a national stage entry of PCT/EP2020/078590 filed Oct. 12, 2020, under the International Convention and claiming priority over French Patent Application No. FR1912294 filed Oct. 31, 2019.

TECHNICAL FIELD

The invention relates to the field of motorized devices for delivering a pressure- and flow rate-regulated gas, such as, notably, a respiratory assistance gas. The device of the invention is a respiratory assistance device incorporating a double-cooling system based on ventilation of the motor equipping the device, while producing a segregation between the respiratory assistance gas delivered to the patient and a cooling air flow for the motor.

The motorized devices for regulated delivery of a gas commonly comprise a chamber housing a motor driving a turbine, such as a vaned rotor for example. The turbine driven by the motor generates an air flow from which the gas is derived, by the addition to the air flow of at least one additive dependent on the composition of the gas to be delivered.

The chamber also forms an aeraulic circuit through which circulates the air flow from which the gas to be delivered is derived. The air flow circulates through the aeraulic circuit from an air inlet, through which the air flow is admitted into the device, to an air outlet through which the gas flow is discharged out of the device.

The air inlet is notably formed by a volute promoting the intake and the dynamics of the air flow to be delivered circulating through the device. The volute is then provided with a connecting member to a duct for the intake of the additive for it to be mixed with the air flow circulating through the volute.

The motor is more specifically a servocontrolled electric motor that makes it possible to regulate the pressure and the flow rate of the air flow circulating through the device, and consequently regulate the pressure and the flow rate of the gas delivered by the device.

One application of such a device is to provide a patient with respiratory assistance. The air flow taken via the turbine is then enriched by the additive such as, notably, oxygen. The oxygen is then introduced into the volute for it to be mixed with the air flow and thus constitute the gas to be delivered to the patient, hereinafter designated patient gas.

The motorization of the device is mounted inside the device while best avoiding any pollution of the patient gas. The rotation speed of the motor is high, for example of the order of 80 000 revolutions/minute. In operation, the motor heats up significantly, and cooling of the motor needs to be provided to increase the performance and the future-proofing of the device and/or to avoid an inopportune rise in temperature of the patient gas.

STATE OF THE ART

It has therefore been proposed to cool the motor by ventilation, as emerges for example from the documents EP2122180 and WO2018/073275 in the name of the present applicant.

According to the document EP2122180, the device is provided with a main turbine generating a main air flow from which the patient gas is derived. The device is also provided with a secondary turbine generating a cooling air flow for the motor. The main turbine and the secondary turbine are mounted at the respective ends of a motor shaft which is driven by the rotor of a servocontrolled electric motor. A chamber forms an aeraulic circuit comprising aeraulic paths through which the main air flow and the cooling air flow circulate. The main air flow is discharged out of the device after having been enriched with oxygen, and the cooling air flow circulates around the motor block for the cooling thereof prior to being discharged out of the device. Such a motor block typically combines the components of the electric motor, being essentially composed of a casing housing a stator and a rotor driving a motor shaft.

According to the document WO2018/073275, the device is provided with a single turbine driven by the rotor of a servocontrolled electric motor, the turbine generating an air flow from which the patient gas is derived. The air flow circulates inside a volute, a fraction of the air flow being diverted out of the volute for cooling the motor. Said fraction of the air flow circulates between the rotor and the stator of the motor, then is discharged out of the device through an air outlet which is assigned to it, preventing its return into the patient gas discharged out of the device.

However, the solutions proposed by the prior art are not fully satisfactory and warrant improvement to best address the structural and functional demands of such respiratory assistance devices.

It has been more particularly found that the solutions proposed by the prior art for cooling the motor equipping the device do not make it possible to provide ventilation of the motor over wide ranges of regulation of the flow rate and/or of the pressure of the air flow or flows circulating through the device. This presents the drawback that certain operating ranges of the motor induce consequential heating thereof and consequently a reduced lifetime thereof.

The result thereof is that there are potential operating ranges of the motor that are proscribed, notably involving operation of the motor providing a flow of patient gas with low flow rate and high pressure, which are, for example, particularly useful for neonatal use or pediatric use.

SUMMARY OF THE INVENTION

The subject of the invention is a motorized respiratory assistance device incorporating a cooling system based on ventilation of the motor equipping the device.

The aim of the invention is to provide a cooling of the motor equipping the device which allows it to be used over a wide range of operating conditions, including over extreme operating ranges such as, for example, for the delivery of a flow of patient gas with low flow rate and high pressure.

One objective of the invention is to provide a cooling of the motor which is particularly effective, in order to limit the heating thereof in operation and thus increase its lifetime.

One notable aim is to obtain an optimized cooling of the motor that makes it possible to safeguard it from degradation resulting from consequential heating of the motor in operation, while maintaining the performance of the motor over the long term and with total reliability.

One ancillary objective of the invention is to obtain a cooling of the motor without affecting the quality of the patent gas. One notable aim is to organize the motor cooling modalities while avoiding soiling the gas delivered to the patient following the ventilation thereof.

Another ancillary objective of the invention is to limit the footprint and/or the weight of the device, in particular by equipping it with a motor cooling system which is simple and not bulky. Notable targets are:

to limit the number of components of the device and to facilitate the obtaining thereof and/or the assembly thereof on the device, without affecting the resulting quality of the device or its future-proofing and/or without affecting its performance, and/or to facilitate the incorporation of the cooling system inside the device and/or avoid cluttering the space surrounding a volute equipping the device, through which volute the air flow from which the patient gas is derived circulates. One notable aim is to clear the environment of the volute to facilitate its connection to an intake duct for at least one additive, including notably at least oxygen, and/or to a duct for conveying the patient gas to the patient.

Another objective of the invention is to allow use of the device with a wide range of input in terms of desired quality of at least one additive to the patient gas, such as oxygen with high concentration possibly extending up to 100%. A notable target is to organize the device so as to preserve the motor from contact with said at least one additive which is potentially aggressive for the motor, such as oxygen in particular, to protect it from oxidation or, more generally, from chemical attack by the additive.

Another objective of the invention is to be able to perform potentially sustained maintenance operations on the device for the cleaning and/or purifying thereof by at least one potentially aggressive disinfectant product. Degradation of the components of the device by the disinfectant product, notably with regard to the motor, must consequently be avoided.

For this, the invention proposes cooling the motor by one and the same cooling air flow, first of all inside then outside the motor, while producing a segregation between this cooling flow and the main air flow from which the patient gas is derived by an independent organization of the aeraulic paths followed by these flows. The internal cooling is effected between the stator and the rotor of the motor, while the cooling outside the motor is established around the casing which houses the motor.

Such double cooling is then exclusively provided by the cooling air flow of the motor which circulates successively inside the motor between the rotor and the stator, then outside the motor around the casing jacketing the motor. The cooling of the motor is thus optimized as a result of the corresponding successive heat exchanges.

The segregation between the secondary aeraulic path and the main aeraulic path is formed by a partitioning between said paths. The air leaks that infiltrate into the space dedicated to the free rotation of the motor shaft are collected between the motor block and said partitioning. The air leaks from the cooling air flow and the air leaks from the main air flow are then drained by the cooling air flow circulating around the motor block, until they are discharged out of the device jointly with the cooling air flow.

More specifically, the invention proposes a motorized respiratory assistance device with integrated cooling system, of the device type comprising an enclosure forming a compartment delimited by a jacket housing a motor block. The motor block comprises a casing receiving at least a rotor and a stator forming a motor driving at least two turbines mounted at the respective axial ends of a motor shaft driven by the rotor.

Said turbines are composed at least of a main turbine generating a main air flow from which a patient gas is derived and a secondary turbine generating a cooling air flow for the motor. The enclosure forms an aeraulic circuit composed at least of two aeraulic paths composed of at least one main aeraulic path conveying the main air flow and at least one secondary aeraulic path conveying the cooling air flow and each comprising an air inlet for the turbines to the inside of the device and an air outlet to the outside of the device.

In this type of device, the invention proposes segmenting the secondary aeraulic path into two portions placed successively in aeraulic communication with one another, including a portion internal to the motor and an outer portion surrounding the motor block. Thus, in a device of the type targeted above, the secondary aeraulic path comprises inner and outer portions in which the cooling flow circulates successively in opposite directions: an inner portion for circulation of the cooling air flow originating from the corresponding air inlet and which extends inside the motor between the stator and the rotor; and an outer portion which extends, parallel to the inner portion, inside an annular space formed around the motor block between the casing of the motor block and the jacket of the enclosure to the corresponding air outlet formed in this jacket on the side of the cooling air inlet.

Furthermore, the main aeraulic path and the secondary aeraulic path are separated from one another by a partitioning formed between them, said partitioning separating the circulation of the main air flow and the circulation of the cooling air flow inside the device. The main air flow is then exclusively dedicated to the delivery of the patient gas and the cooling air flow is exclusively dedicated to the double cooling of the motor.

Such an architecture of the secondary aeraulic path provides dual cooling of the motor by the cooling air flow, including a cooling internal to the motor between the rotor and the stator and then an external cooling of the motor around the casing which houses it. The cooling of the motor obtained is powerful based on its dual ventilation by just the cooling air flow. A passage of the main air flow through the motor is thus prohibited to avoid deterioration of it by a damaging additive—oxygen in particular—which is contained in the patient gas and/or by a cleaning and/or purifying agent during a maintenance operation on the device. In parallel, pollution of the main air flow by the cooling air flow is also avoided.

The optimization of the cooling of the motor that is thus obtained makes it possible to preserve it and increase its lifetime, and do so by allowing it to operate, including according to extreme ranges of pressure and flow-rate regulation of the main air flow, such as, notably, ranges of regulation with low flow rate and high pressure of the main air flow for neonatal use or pediatric use of the device for example.

The assigning of the cooling air flow exclusively to the cooling of the motor and of the main air flow exclusively to the respiratory assistance of a patient, makes it possible to avoid any soiling of the main air flow by the cooling air flow by segregation between the main aeraulic path and the secondary aeraulic path, such as, notably, via a partitioning formed between them that can be of simple structure.

The forced circulations by the turbines respectively of the main air flow and of the cooling air flow to the outside of the device are segregated. Air leaks respectively from the main air flow and from the cooling air flow are then collected and mixed in a chamber which is dedicated to them and which is in aeraulic communication with the outer portion of the secondary aeraulic path. The collected and mixed air leaks are then drained by the cooling air flow circulating around the motor block, and are discharged out of the device without risk of degradation of the motor.

Preferably, a volume interfaced between the motor block and said partitioning forms a chamber for collection and mixing between, on the one hand, air leaks from the main air flow and originating from the main aeraulic path by passing through said partitioning and, on the other hand, air leaks from the cooling air flow and originating from the motor block. The chamber is in aeraulic communication via at least one air passage with the outer portion of the secondary aeraulic path, such that said air leaks are drained out of the chamber, notably in the form of a flow of mixed air leaks, to the inside of the outer portion of the secondary aeraulic path by the cooling air flow discharged out of the motor block. The cooling air flow and said air leaks are then jointly discharged out of the device via the air outlet of the secondary aeraulic path.

Advantageously, the cooling air flow is admitted into the inside of the inner portion of the secondary aeraulic path, then is discharged out of the motor block to the outer portion of the secondary aeraulic path through at least one second aperture passing through the wall of the casing of the motor block.

According to one embodiment, said at least second aperture passes radially through the wall of the casing of the motor block and is disposed at a short axial distance from the partitioning, lying as close as possible to the partitioning. It is also understood that the relative axial and radial notions are identified with respect to the direction of axial extension of the motor shaft inside the device. The chamber is axially formed between the motor block and the partitioning by emerging axially on the outer portion of the secondary aeraulic path.

This makes it possible to optimize the axial extension of the outer portion of the secondary aeraulic path. This also makes it possible to promote the driving of the air leaks out of the chamber via said at least one air passage—by the cooling air flow discharged out of the motor block—to the outer portion of the secondary aeraulic path.

In order to maximize the reduction of the infiltration of the air leaks, sealing members made of thermostable polymer material are mounted around the motor shaft with a minimal play, and are composed at least of a sealing member secured to the partitioning on the side of the volute, and of sealing members secured to rolling bearings mounted on the casing outside of the motor block.

According to one embodiment, the secondary turbine is housed inside a cavity for the intake of the cooling air flow inside the motor block, via the air inlet of the secondary aeraulic path. The cavity is isolated from the outer portion of the secondary aeraulic path and is open on the inside of the motor block via at least one air passage formed through the casing.

The cavity housing the secondary turbine forces the cooling air flow admitted inside the device to circulate toward the inner portion of the secondary aeraulic path, prior to the circulation of the cooling air flow through the outer portion of the secondary aeraulic path.

Notably, according to one embodiment, the cavity is delimited between the peripheral wall of the jacket and a crown ring radially surrounding the casing of the motor block. The air outlet of the secondary aeraulic path is formed radially through the jacket axially interposed between the crown ring and said at least one second aperture passing through the wall of the casing of the motor block. In the axial extension of the device, the air outlet of the secondary aeraulic path is notably formed as close as possible to the crown ring and at a significant separating distance from the second aperture, to best increase the extension of the outer portion of the secondary aeraulic path.

For example, again according to another embodiment, the cavity is formed by the inner volume of a caisson which is mounted axially on the casing and which forms the air inlet of the secondary aeraulic path. The caisson is disposed inside the compartment receiving the motor block in axial extension of the casing. The caisson is notably added and fixed to the casing by tight sealing between the caisson and the casing.

According to one embodiment, the caisson is configured in cone form of which the largest outlet is oriented toward the motor and of which the smallest outlet is prolonged axially by an air inlet duct incorporated in the caisson. The air inlet duct passes axially by fit through a wall of the jacket, forming the air inlet of the secondary aeraulic path and forming an axial centering member of the motor block inside the compartment.

According to one embodiment, the air outlet of the secondary aeraulic path is formed by the outward emergence from the enclosure of an air outlet duct incorporated in the jacket.

According to one embodiment, the air inlet duct and the air outlet duct of the secondary aeraulic path are disposed at a first axial end of the device which is opposite its other second axial end at which the main aeraulic path is formed between the air inlet and the air outlet that it comprises.

According to one embodiment, the enclosure comprises a volute housing the main turbine and delimiting the main aeraulic path. Said volute forms the air inlet and the air outlet of the main aeraulic path and can be provided with at least one connecting member to a duct for the intake of an additive inside the volute.

According to one embodiment, at least one wall delimiting the volute forms the separating partitioning between the main aeraulic path and the secondary aeraulic path. Said wall forming the partitioning incorporates said connecting member and delimits between them, on the one hand, the volute and the air outlet of the main air flow out of the device which is incorporated in the volute, and, on the other hand, the compartment receiving the motor block.

DESCRIPTION OF THE FIGURES

The invention will be better understood on reading the following detailed description of exemplary embodiments of the invention, in relation to the following figures of the attached plates which represent.

DETAILED DESCRIPTION

The figures and their nonlimiting detailed description explain the invention according to particular modalities which are not restrictive as to the scope of the invention as defined by the claims. The figures and their detailed description can be used to better understand and define the invention, if necessary, in relation to the general description which has just been given thereof.

Figure 1:
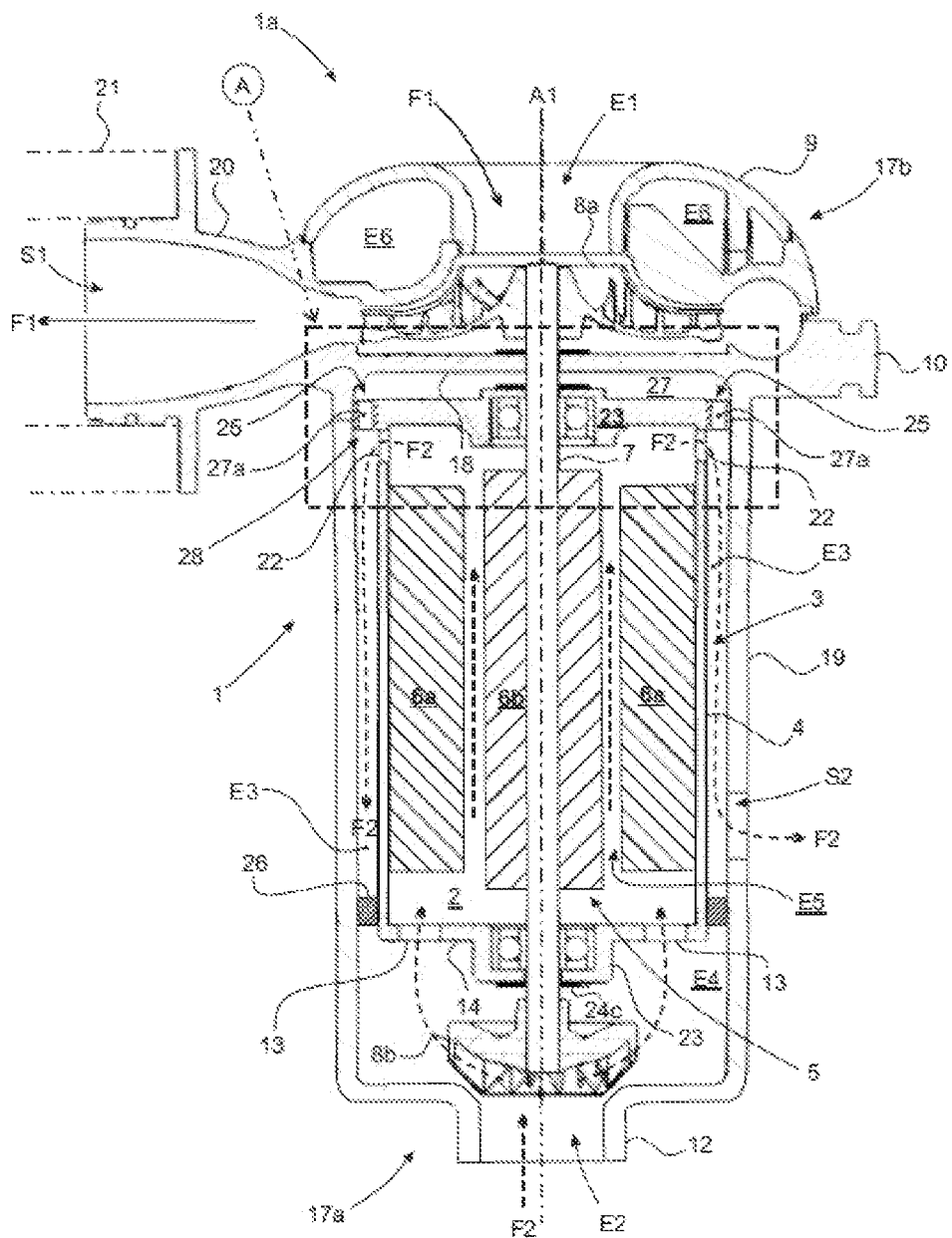
FIG. 1, an illustration in axial cross-section of a motorized respiratory assistance device with integrated cooling system, according to a first exemplary embodiment of the invention.
Figure 2:
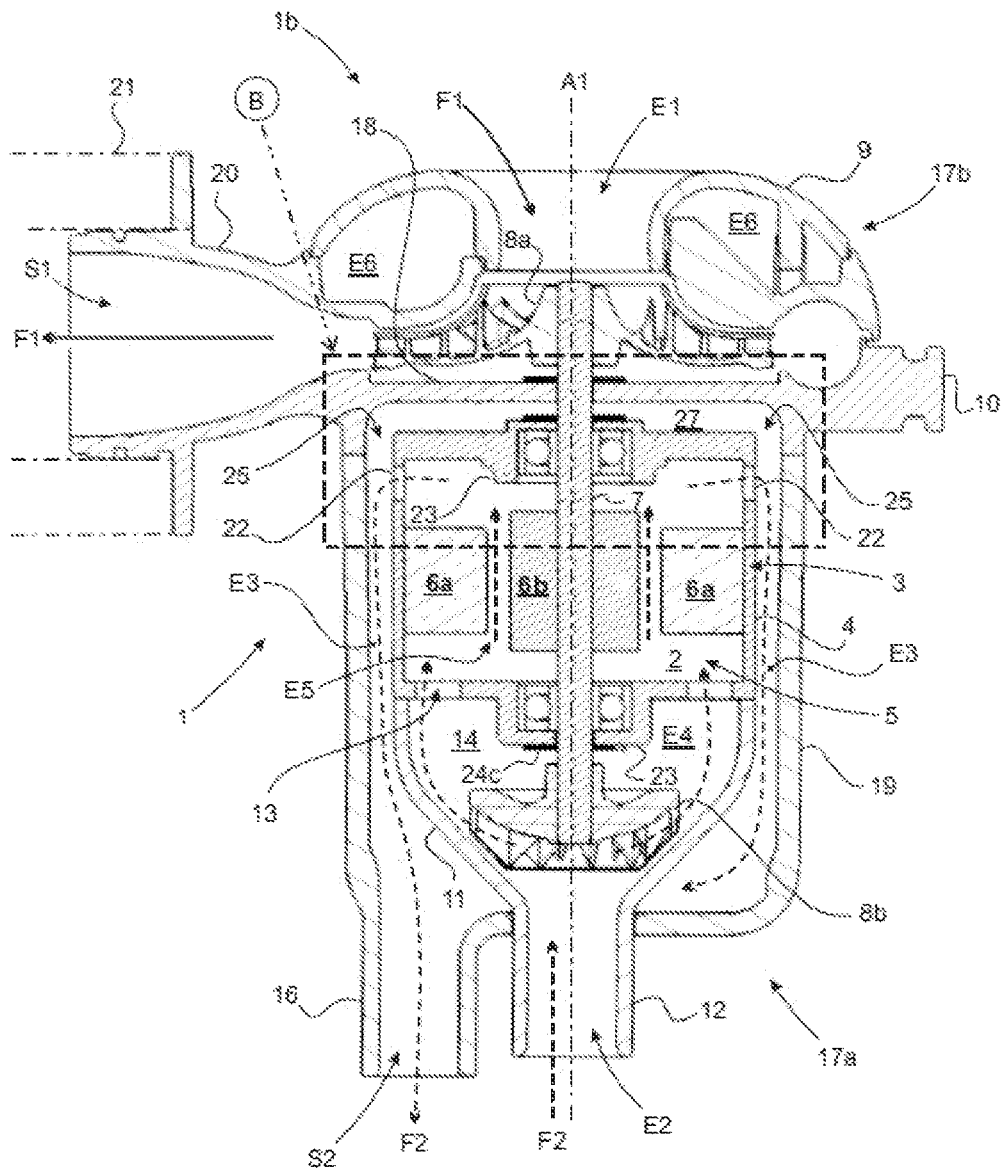
FIG. 2, an illustration in axial cross-section of a motorized respiratory assistance device with integrated cooling system, according to a second exemplary embodiment of the invention.

In FIG. 1 and FIG. 2, motorized devices 1a, 1b for the regulated delivery of a gas are applied to the respiratory assistance of a patient. The devices 1a, 1b have an axial extension A1 and form an enclosure 1 formed essentially by a volute 9 and by a jacket 19 assembled axially together. The jacket 19 delimits, inside the devices 1a, 1b, a compartment 2 receiving a motor block 3. The motor block 3 comprises a casing 4 housing an electric motor 5, comprising a stator 6a and a rotor 6b rotationally driving a motor shaft 7, and mounted on rolling bearings 23 about this motor shaft. It is understood that the axial extension of the devices 1a, 1b is identified by the orientation of the axis A1 of extension of the motor shaft 7.

The devices 1a, 1b are organized to generate two air flows F1, F2. A main air flow F1 is dedicated to the respiratory assistance of a patient and a cooling air flow F2 is dedicated to the cooling of the motor 5 after it has been started up. To this end, turbines 8a, 8b are mounted at the respective axial ends of the motor shaft 7, being, for example, each formed by at least one vaned rotor.

A secondary turbine 8b generating the cooling air flow F2 is mounted at a first of the axial ends of the motor shaft 7. A main turbine 8a generating the main air flow F1 is mounted at the other, second of the axial ends of the motor shaft 7. Following a regulated activation of the motor 5, the motor shaft 7 is driven in rotation via the rotor 6b of the motor 5. The rotating of the motor shaft 7 makes it possible to drive the main turbine 8a in rotation to generate the main air flow F1 and the secondary turbine 8b to generate the cooling air flow F2.

The main turbine 8a is housed inside a volute 9 that the enclosure 1 comprises. The volute 9 forms a first air inlet E1 for the intake of the main air flow F1 inside the devices 1a, 1b and a first air outlet S1 for the discharging, out of the devices 1a, 1b, of a patient gas derived from the main air flow F1 which is enriched with oxygen. The oxygen is introduced into the main air flow F1 inside the volute 9, via a duct for the intake of oxygen (not represented) inside the enclosure 1. Furthermore, a suspension interface 10 for the main turbine 8a attenuates the vibrations and noises.

A main aeraulic path E1, E6, S1 conveying the main air flow F1 inside the devices 1a, 1b is delimited by the internal volume E6 of the volute 9 which extends at the interface between the first air inlet E1 and the first air outlet S1 formed by the volute 9. The main aeraulic path E1, E6, S1 is delimited by the outer enclosure of the volute 9 and by a partitioning 18 which is incorporated in the volute 9. The partitioning 18 isolates the internal volume E6 of the volute 9 from the compartment 2 receiving the motor block 3. The patient gas is delivered to the patient to provide him or her with respiratory assistance, via a duct 21 connected to a fitting 20 which is incorporated in the volute 9 and which forms the first air outlet S1.

The secondary turbine 8b is housed inside a cavity E4 for the intake of the cooling air flow F2 to the inside of the devices 1a, 1b. The cavity E4 is open on a second air inlet E2 for the intake of the cooling air flow inside the devices 1a, 1b. The second air inlet E2 is formed by the outward emergence from the device 1a, 1b of an air inlet duct 12 coaxial to the motor shaft 7. The cavity E4 is also open on the internal volume of the motor block 3, via first apertures 13 of axial orientation which are formed through the wall of the casing 4 forming an axial separating partition 14 between the cavity E4 and the motor 5.

The cooling air flow F2 admitted into the devices 1a, 1b via the second air inlet E2 circulates inside the cavity E4 and then is admitted into the internal volume of the motor block 3 via the first apertures 13. A first cooling internal to the motor 5 is thus produced by the cooling air flow F2 flowing between the rotor 6b and the stator 6a of the motor 5.

Then, the cooling air flow F2 is discharged out of the motor block 3 through radial second apertures 22 that the wall of the casing 4 includes in its zone of axial extension. The cooling air flow F2 is then admitted into an annular space E3 surrounding the motor block 3 which is formed inside the compartment 2 between the jacket 19 and the peripheral wall of the casing 4.

The cooling air flow F2 then circulates around the motor block 3 until it is discharged out of the devices 1a, 1b via a second air outlet S2 that the jacket 19 includes. A second, external cooling of the motor 5 is thus produced by the cooling air flow F2 flowing inside the compartment 2 around the motor block 3.

A secondary aeraulic path E2, E4, 13, E5, 22, E3, S2 conveying the cooling air flow F2 inside the devices 1a, 1b is thus delimited inside the compartment 2. The secondary aeraulic path E2, E4, 13, E5, 22, E3, S2, extends more specifically from the second air inlet E2 to the second air outlet S2, in successively comprising—in the direction of circulation of the cooling air flow F2 inside the devices—the cavity E4, the first apertures 13, the internal volume of the motor block 3, the second apertures 22 and the annular space E3 surrounding the motor block 3.

More particularly, the secondary aeraulic path comprises an inner portion E5 formed by the internal volume of the motor 5 and an outer portion E2, E4, 13, 22, E3, S2 outside the motor 5. Said outer portion is composed of the second air inlet E2, the cavity E4, the first apertures 13, the second apertures 22, the annular space E3 surrounding the motor block 3 and the second air outlet S2. To best increase the external cooling of the motor 5, the circulation of the cooling air flow F2 around the motor block 3 is optimized. The second apertures 22 are formed radially through the peripheral wall of the casing 4 at a short axial distance from the partitioning 18 and at a wide axial distance from the second air outlet S2 of the secondary aeraulic path E2, E4, 13, E5, 22, E3, S2.

The cooling of the motor 5 obtained is thus powerful through the dual circulation of the cooling air flow F2 firstly inside the motor 5 between the rotor 6b and the stator 6a then, secondly, around the motor block 3, prior to it being discharged out of the devices 1a, 1b. The cooling air flow F2 is specifically dedicated to the cooling of the motor 5 by being taken from the environment outside the devices 1a, 1b, which is free of agents likely to damage the components of the motor 5.

The main air flow F1 is propelled by the main turbine 8a inside the volute 9 from the first air inlet E1 to the first air outlet S1. The cooling air flow F2 is propelled by the secondary turbine 8b from the second air inlet E2 inside and then outside the motor block 3 to the second air outlet S2.

The partitioning 18 interfaced between the volute 9 and the compartment 2 housing the motor block 3 provides a segregation between the respective paths—main aeraulic path and secondary aeraulic path—of forced circulations of the main air flow F1 and of the cooling air flow F2 through the devices 1a, 1b. Such a segregation provides an effective internal and external cooling of the motor 5, while avoiding passage inside the compartment 2 of the main air flow F1, the circulation of which is forced only inside the volute 9. Conversely, also avoided is passage to the inside of the volute 9 of the cooling air flow F2, the circulation of which is forced only inside the compartment 2.

The result of that is that the possibility of degradation of the motor 5 occurring, possibly induced by excessive heating of the motor 5 and/or by a damaging agent conveyed by the main air flow F1—oxygen or maintenance agent for the devices 1a, 1b in particular—whose circulation is forced only through the volute 9, is avoided. Conversely, also avoided is the possibility of soiling of the main air flow F1 being induced by a possible pollution of the cooling air flow F2 following its passage inside the motor block 3, the forced circulation of the cooling air flow F2 taking place only inside the compartment 2.

Figure 3:
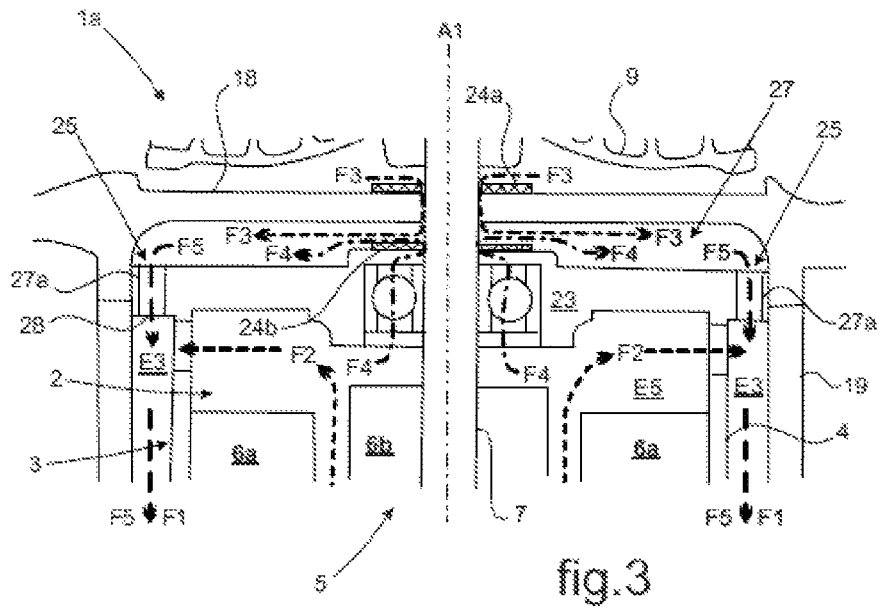
FIG. 3, an enlargement (A) of FIG. 1, illustrating in axial cross-section modalities for managing air leaks circulating through the device represented in FIG. 1, and FIG. 4, an enlargement (B) of FIG. 2, illustrating in axial cross-section modalities for managing air leaks circulating through the device represented in FIG. 2.
Figure 4:
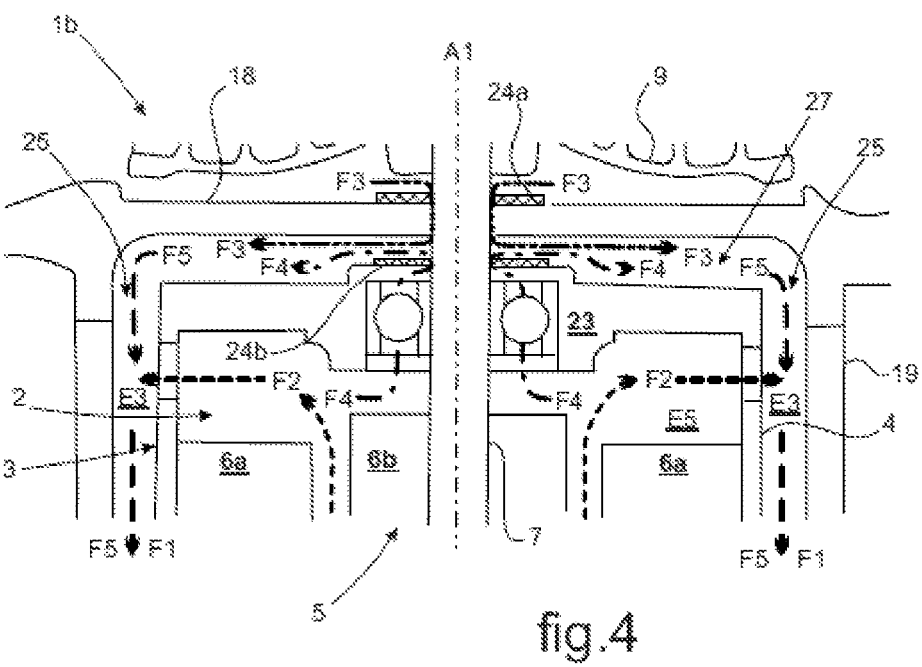

As can be seen more particularly in FIG. 3 and FIG. 4, account is also taken of the fact that the motor shaft 7 passes through the partitioning 18 and the casing 4 of the motor block 3. Air leaks F3 from the main air flow F1 can infiltrate between the motor shaft 7 and the partitioning 18 from the volute 9 to the compartment 2. Conversely, air leaks F4 from the cooling air flow F2 can infiltrate between the motor shaft 7 and the partitioning 18 from the compartment 2 to the volute 9.

The possibility of the air leaks F3 from the main air flow F1 degrading the motor 3, and/or of the air leaks F4 from the cooling air flow F2 polluting the main air flow F1 must be avoided.

To reinforce the strength of the segregation between the main aeraulic path E1, E6, S1 and the inner portion E5 of the secondary aeraulic path, the air leaks F3, F4 are collected and drained out of the devices 1a, 1b by preventing their passage inside the motor block 3.

More particularly, the air leaks F3, F4 infiltrating between the motor shaft 7 and the partitioning 18 and/or the casing 4 are collected inside a chamber 27 extending axially between the motor block 3 and the partitioning 18. The air leaks F3 originating from the volute 9 and the air leaks F4 originating from the motor block 3 are then mixed inside the chamber 27. The chamber 27 is in aeraulic communication with the annular space E3 surrounding the motor block 3, via at least one air passage 25, such that the mixture of the air leaks F3, F4 is driven—in the form of a flow of mixed air leaks F5—by the cooling air flow F2 discharged out of the motor block 3, via the second apertures 22, and circulating around the motor block 3.

The air leaks F3, F4 are then mingled with the cooling air flow F2 circulating outside the motor block 3 without the risk of contact between the air leaks F3, F4 and the motor 5. The air leaks F3, F4 and the cooling air flow F2 are then discharged jointly out of the devices 1a, 1b via the second air outlet S2.

In order to minimize the infiltration of said air leaks F3, F4 between the volute 9 and the compartment 2, sealing members made of polymer material 24a, 24b, 24c (FIGS. 1 and 2)—such as, for example, washers made of elastomer or of silicone or other thermostable polymer—are advantageously provided. The sealing members 24a, 24b, 24c are mounted around the motor shaft 7 with a minimal play. A first sealing member 24a is secured to the partitioning 18 on the side of and toward the inside of the volute 9.

Second and third sealing members 24b, 24c are placed outside the motor block 3 and secured on the rolling bearings 23 to form an obstacle to prevent a lubricant, routinely present in the rolling bearings 23 interfaced between the motor shaft 7 and the casing 4 of the motor block 3, from escaping out of the motor block 3.

According to the embodiment of the device 1a illustrated in FIG. 1, the cavity E4 housing the secondary turbine 8b is formed by an internal volume of the compartment 2, which extends interposed axially between the motor block 3 and the second air inlet E2. The cavity E4 is delimited between the wall of the jacket 19 and a crown ring 26 radially surrounding the casing 4 of the motor block 3 at its end oriented toward the second air inlet E2. The crown ring 26 extends diametrically between the casing 4 and the wall of the jacket 19 in its axial extension part, forcing the passage of the cooling air flow F2 inside the motor block 3 and forming an obstacle to the passage around the motor block 3 of the cooling air flow F2 admitted into the compartment 2.

The air inlet duct 12 is formed by the wall of the jacket 19. The second air outlet S2 is formed radially through the jacket 19 in axial proximity to the crown ring 26 and axially distanced from the second apertures 22 passing through the wall of the casing 4, to optimize the outer cooling of the motor 3 during the circulation of the cooling air flow F2 around the motor block 3. The second air outlet S2 can be formed by an air outlet duct of radial extension incorporated in the jacket 19.

Referring also to FIG. 3, several air passages 25 for discharging air leaks F3, F4 out of the chamber 27—in the form of the flow of mixed air leaks F5—are formed by a plurality of channels 27a. Said channels 27a are formed axially through the wall of the casing 4 in its part oriented toward the chamber 27 which extends diametrically between the peripheral wall of the jacket 19 and the peripheral wall of the casing 4. More particularly, the channels 27a are distributed radially through an annular portion 28 of the wall of the casing 4 which extends diametrically inside the annular space E3 surrounding the motor block 3.

According to the embodiment of the device 1b illustrated in FIG. 2, the cavity E4 housing the secondary turbine 8b is formed by the internal volume of a caisson 11 housed inside the compartment 2 by being axially secured to the casing 4 of the motor block 3. The caisson 11 is arranged as a funnel, by comprising a cone axially extended by the air inlet duct 12 via which the cooling air flow F2 is admitted into the device 1b.

The air inlet duct 12 passes, by tight fit, through the wall of the enclosure 1, forming a centering member for the motor block 3 inside the compartment 2. An air outlet duct 16 is formed by the wall of the jacket 19 by being oriented according to the axial orientation of the device 1b. The air outlet duct 16 emerges out of the enclosure 1 to form the second air outlet S2, via which the cooling air flow F2 is discharged out of the device 1b.

Referring also to FIG. 4, the air passage 25 for discharging of the air leaks F3, F4 out of the chamber 27 is formed by an outlet onto the chamber 27 from the annular space E3 surrounding the motor block 3. The driving of the air leaks F3, F4 mixed inside the chamber 27 by the cooling air flow F2 circulating around the motor block 3 is thereby promoted.

The invention is not limited to the examples described and represented. Thus, various complementary arrangements of the device 1a, 1b stemming from the invention can be provided.

For example, the cooling air flow F2 can be discharged via several second air outlets equipping the devices 1a, 1b, to increase the flow rate and/or the velocity of the cooling air flow F2 circulating through the devices 1a, 1b.

More particularly concerning the device 1a represented in FIG. 1, several seconds air outlets S2 can for example be formed radially through the wall of the jacket 19. Additionally, the second air outlet or outlets can each be formed by an air outlet duct 16 incorporated in the jacket 19.

Furthermore, regarding the device 1b represented in FIG. 2, several second air outlets S2 can for example be formed axially through the wall of the jacket 19 at the first axial end 17a of the device 1b. The second air outlets S2 are then for example formed by holes of axial extension distributed radially through the wall of the jacket 19, each being free of any said second air outlet duct 16.

Moreover, the annular space E3 which surrounds the motor block 3 and which contributes to the outer portion of the secondary aeraulic path via which the cooling air flow F2 circulates around the motor block 3, can house one or more heat exchange elements between the cooling air flow F2 and the casing 4 of the motor block 3 and/or the jacket 19. Such heat exchange elements are for example composed of openwork fins or for example are even formed by the reinforcement of a metal lattice. The heat exchange elements are notably distributed axially inside the annular space E3 surrounding the motor block 3 and contributing to the secondary aeraulic path, by being placed in contact with the casing 4 of the motor block 3 and with the jacket 19.

Furthermore, the annular space E3 surrounding the motor block 3 via which the cooling air flow F2 circulates around the motor block 3, can be configured as a chicane. Such a chicane makes it possible to increase the path followed by the cooling air flow F2 around the motor block 3. Furthermore, such a chicane can advantageously be composed of said heat exchange elements as previously targeted.

The device 1a, 1b can be equipped with a mechanism for disengaging the drive of the main turbine 8a by the motor shaft 7. Such a disengaging mechanism makes it possible, in the case of a temporary stoppage in the delivery of the patient gas, to maintain the driving of the secondary turbine 8b by the motor 5. The driving of only the secondary turbine 8b can be produced without subjecting the motor 5 to a consequential load to maintain cooling thereof by the cooling air flow F2 as far as a predefined cooling threshold.

Maintaining the cooling of the motor 5 in the event of a stoppage in the delivery of the patient gas makes it possible to rapidly complete the cooling of the motor 5, subject for example to a timer and/or a temperature sensor housed in the motor block 3 and measuring the temperature of the motor 5. The disengaging mechanism can for example be placed inside the motor block 3, by being configured as a jaw-clutching mechanism placed on the motor shaft 7.

The jaw-clutching mechanism can be of the type that can be activated by an electromagnetic control maneuvering the jaw clutch that it comprises, between an active position of engagement and an inactive position of disengagement of the driving of the main turbine 8a by the motor shaft 7.

In addition, the air taken through the second air inlet E2 by the secondary turbine 8b can be cooled prior to its intake into the device 1a, 1b. To this end, the device 1a, 1b can for example be coupled to a heat treatment system for the cooling air flow F2.

The partitioning between the secondary aeraulic path and the main aeraulic path can be produced by any panel, support, wall of suitable form and structure for allowing the optimal segregation between the flows.

Regarding the air outlets S1, S2, they can be composed of one or more apertures formed in the fitting 20, the caisson 11 and/or the jacket 19.

Moreover, the number of turbines is not limited to two: series and/or parallel mountings of several main turbines and/or of several secondary turbines can be implemented.

It will be noted that the application of a device 1a, 1b according to the invention to the respiratory assistance of a patient is not restrictive as to the scope of the invention. Indeed, a device 1a, 1b conforming to the invention in light of its structure and/or of its modalities of operation, can be applied to other motorized devices for the regulated delivery of a gas with integrated cooling system.

It should also be noted that a device 1a, 1b conforming to the invention can be used to treat air circulating through an air conditioning device. The air conveyed to the air conditioning device is formed by the main air flow F1 taken via the volute 9 of a device 1a, 1b according to the invention. The main air flow F1 taken can then be enriched inside the volute 9, by at least one additive such as a purifying agent of the air-conditioning device and/or a fragrant agent.

The invention claimed is:

1. A motorized respiratory assistance device (1a, 1b) with integrated cooling system, the device (1a, 1b) comprising:
    an enclosure (1) forming a compartment (2) delimited by a jacket (19) housing a motor block (3), the motor block (3) comprising a casing (4) receiving at least a rotor (6b) and a stator (6a) forming a motor (5) driving at least two turbines (8a, 8b) mounted at respective axial ends of a motor shaft (7) driven by the rotor (6b), said turbines (8a, 8b) including at least one main turbine (8a) generating a main air flow (F1) from which is derived a patient gas, and a secondary turbine (8b) generating a cooling air flow (F2) for the motor (5),
    the enclosure (1) forming an aeraulic circuit including at least two aeraulic paths having at least one main aeraulic path conveying the main air flow (F1) and at least one secondary aeraulic path conveying the cooling air flow (F2), each comprising an air inlet (E1, E2) for the turbines (8a, 8b) to an inside of the device (1a, 1b) and an air outlet (S1, S2) to an outside of the device (1a, 1b),
    wherein the secondary aeraulic path comprises an inner portion (E4) for circulation of the cooling air flow (F2) originating from the corresponding air inlet (E2) and extending inside the motor (5) between the stator (6a) and the rotor (6b), and an outer portion (E3) extending, parallel to the inner portion (E4), inside an annular space (E3) formed around the motor block (3) between the casing (4) of the motor block (3) and the jacket (19) of the enclosure (1) to the corresponding air outlet (S2) formed in the jacket (19) on a side of the cooling air inlet (E2), the cooling air flow (F2) circulating successively in opposite directions in the inner (E4) and outer (E3) portions, and in that the main aeraulic path (E1, E6, S1) and the secondary aeraulic path (E2, E4, E5, 22, E3, S2) are separated from one another by a partitioning (18) formed between them, said partitioning (18) separating circulation of the main air flow (F1) and circulation of the cooling air flow (F2) inside the device (1a, 1b).

2. The device (1a, 1b) as claimed in claim 1, wherein a volume interfaced between the motor block (3) and said partitioning (18) forms a chamber (27) for collecting and mixing between, on one hand, air leaks (F3) from the main air flow (F1) and originating from the main aeraulic path (E1, E6, S1) by passing through said partitioning (18) and, on an other hand, air leaks (F4) from the cooling air flow (F2) and originating from the motor block (3), and in that the chamber (27) is in aeraulic communication via at least one air passage (25) with the outer portion (E3, S2) of the secondary aeraulic path (E2, E4, E5, 22, E3, S2), such that said air leaks (F3, F4) are drained out of the chamber (27)

to an inside of the outer portion (E3, S2) of the secondary aeraulic path (E2, E4, E5, 22, E3, S2) by the cooling air flow (F2) discharged out of the motor block (3), the cooling air flow (F2) and said air leaks (F3) being jointly discharged out of the device (1a, 1b) via the air outlet (S2) of the secondary aeraulic path (E2, E4, E5, 22, E3, S2).

3. The device (1a, 1b) as claimed in claim 2, wherein at least a second aperture (22) passes radially through a wall of the casing (4) of the motor block (3) and is disposed at a short axial distance from the partitioning, and in that the chamber (27) is axially (A1) formed between the motor block (3) and the partitioning (18) by emerging axially (A1) on the outer portion (E3, S2) of the secondary aeraulic path (E2, E4, E5, 22, E3, S2).

4. The device (1a, 1b) as claimed in claim 1, wherein the cooling air flow (F2) is admitted into the inner portion (E2, E4, E5, 22) of the secondary aeraulic path (E2, E4, E5, 22, E3, S2) then is discharged out of the motor block (3) to the outer portion (E3,S2) of the secondary aeraulic path through at least one aperture (22), called a second aperture, passing through a wall of the casing (4) of the motor block (3).

5. The device (1a) as claimed in claim 4, wherein a cavity is delimited between a peripheral wall of the jacket (19) and a crown ring (26) radially surrounding the casing (4) of the motor block (3), the air outlet (S2) of the secondary aeraulic path (E2, E4, E5, 22, E3, S2) being formed radially through the jacket (19) by axial interposition between the crown ring (26) and said at least second aperture (22) passing through the wall of the casing (4) of the motor block (3).

6. The device (1a, 1b) as claimed in claim 1, wherein sealing members (24a, 24b, 24c) are mounted around the motor shaft (7) with a minimal play, and are composed at least of a sealing member (24a) secured to the partitioning (18) on a side of a volute (9), and of sealing members (24b, 24c) secured to rolling bearings (23) mounted on the casing (4) outside of the motor block (3).

7. The device (1a, 1b) as claimed in claim 1, wherein the secondary turbine (8b) is housed inside a cavity (E4) for intake of the cooling air flow (F2) to the inside of the motor block, via the air inlet (E2) of the secondary aeraulic path (E2, E4, E5, 22, E3, S2), the cavity (E4) being isolated from the outer portion (E3,S2) of the secondary aeraulic path (E2, E4, E5, 22, E3, S2) and being open on the inside of the motor block (3) via at least one other aperture (13), called a first aperture, formed through the casing (4).

8. The device (1b) as claimed in claim 7, wherein the cavity (E4) is formed by an internal volume of a caisson (11) which is mounted axially on the casing (4) and which forms the air inlet (E2) of the secondary aeraulic path (E2, E4, E5, 22, E3, S2), the caisson (11) being disposed inside the compartment (2) receiving the motor block (3) in axial extension of the casing (4).

9. The device (1b) as claimed in claim 8, wherein the caisson (11) is configured in cone-form, a largest outlet of which is oriented toward the motor (5) and a smallest outlet of which is prolonged axially by an air inlet duct (12) incorporated in the caisson (11), the air inlet duct (12) passing axially by fit through a wall of the jacket (19), forming the air inlet (E2) of the secondary aeraulic path (E2, E4, E5, 22, E3, S2) and forming an axial centering member of the motor block (3) inside the compartment (2).

10. The device (1b) as claimed in claim 9, wherein an air outlet duct (12) and the air outlet duct (16) of the secondary aeraulic path (E2, E4, E5, 22, E3, S2) are disposed at a first axial end (17a) of the device opposite a second axial end (17b) at which the main aeraulic path (E1, E6, S1) is formed between the air inlet (E1) and the air outlet (E2).

11. The device (1a, 1b) as claimed in claim 1, wherein the air outlet (S2) of the secondary aeraulic path is formed by an outward emergence from an enclosure of an air outlet duct (16) incorporated in the jacket (19).

12. The device (1a, 1b) as claimed in claim 1, wherein the enclosure (1) comprises a volute (9) housing the main turbine (8a) and delimiting the main aeraulic path (E1, E6, S1), said volute (9) forming the air inlet (E1) and the air outlet (S1) of the main aeraulic path and being provided with at least one connecting member (10) to a duct for an intake of an additive to an inside of the volute (9).

13. The device (1a, 1b) as claimed in claim 12, wherein at least one wall delimiting the volute (9) forms the partitioning (18) between the main aeraulic path (E1, E6, S1) and the secondary aeraulic path (E2, E4, E5, 22, E3, S2), said wall forming the partitioning (18) incorporating said connecting member (10) and delimiting between them, on one hand, the volute (9) and the air outlet (S1) for the main air flow (F1) out of the device which is incorporated in the volute (9) and, on an other hand, the compartment (2) receiving the motor block (3).

* * * * *